(12) United States Patent  (10) Patent No.: US 7,261,703 B2
Lampropoulos et al.  (45) Date of Patent: Aug. 28, 2007

(54) VASCULAR BLOOD CONTAINMENT DEVICE

(75) Inventors: Fred P. Lampropoulos, Sandy, UT (US); Brian W. Stevens, Pleasant Grove, UT (US); Gar Hendry, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 290 days.

(21) Appl. No.: 10/424,886

(22) Filed: Apr. 28, 2003

(65) Prior Publication Data

US 2004/0215146 A1  Oct. 28, 2004

(51) Int. Cl.
*A61M 5/178* (2006.01)
(52) U.S. Cl. .................. 604/168.01; 604/900
(58) Field of Classification Search .......... 604/164.01, 604/168.01, 187, 264, 272, 900
See application file for complete search history.

(56) References Cited

U.S. PATENT DOCUMENTS

| 5,295,970 | A | | 3/1994 | Clinton et al. .............. 604/168 |
| 5,501,671 | A | | 3/1996 | Rosen et al. ................. 604/168 |
| 5,820,596 | A | | 10/1998 | Rosen et al. ................. 604/108 |
| 5,980,492 | A | | 11/1999 | Rosen et al. ................. 604/164 |
| 5,984,895 | A | * | 11/1999 | Padilla et al. .......... 604/168.01 |

* cited by examiner

*Primary Examiner*—Kevin C. Sirmons
*Assistant Examiner*—Laura C. Schell
(74) *Attorney, Agent, or Firm*—Workman Nydegger

(57) ABSTRACT

The present invention is directed to a vascular blood containment that allows a user to determine whether a blood vessel has been accessed and which provides access to the vessel. The vascular blood containment device includes a compression seal having increased reliability. The seal permits the passage of gas but prevents the passage of liquid. A valve providing access to a blood vessel through the blood containment device is configured to conform to an inner profile formed around a bore of the distal end of the outer housing. The configuration of the device permits the blood containment chamber to fill properly when the distal end of the blood containment device is positioned below the proximal end of the device.

27 Claims, 8 Drawing Sheets

VASCULAR BLOOD CONTAINMENT DEVICE

BACKGROUND OF THE INVENTION

1. The Field of the Invention

The present invention generally relates to vascular entry devices. More particularly, the invention relates to blood containment devices for use with a vascular entry needle to provide visual confirmation that the needle tip has entered into a blood vessel and to allow for the introduction of an enlongated medical instrument through the device.

2. The Relevant Technology

It is a common medical procedure to insert a hollow needle into a patient's blood vessel for the purpose of either withdrawing blood or introducing a drug, guide wire, guide catheter, or the like into the blood vessel. One difficulty with such procedures, however, is determining when the tip of the needle is properly placed within the selected blood vessel. Another concern is that unless the blood is contained, vascular pressure, and arterial pressure in particular, can force a leakage or spray of blood through the opposite end of the needle. This can create a risk to medical personnel of exposure to blood-borne viruses, such as hepatitis and HIV, that may be present in the patient's blood.

The problems of blood containment and confirming proper needle placement are particularly applicable during the procedure for introducing a guide wire, catheter, or the like into a patient's artery for carrying out procedures in or around the patient's heart. Such catheterization involves first creating access to the selected artery using a vascular entry needle of sufficient bore, and then inserting a guide wire, guide catheter, or other catheter apparatus through the needle and into the selected artery. Often, the guide wire is first inserted and located in a desired position, after which the catheter is inserted over the guide wire to the desired position. Self-guiding catheters may also be inserted without first using a guide wire. After the catheter apparatus has been placed into the desired position, the vascular entry needle can then be removed by sliding it backwards over and off the proximal end of the guidewire.

In performing a catheterization procedure, as noted above, it is crucial that the vascular entry needle be properly positioned within the selected blood vessel. When an ordinary needle is used, entry of the needle tip into the blood vessel is indicated by the escape of blood at the proximal end of the needle. However, this has the attendant contamination problems as noted above.

Another problem is that, during positioning, the needle can accidentally be pulled out of the blood vessel or pushed through the opposite side of the vessel wall, which defeats the catheterization procedure. Accordingly, it is important after the needle tip first enters the blood vessel to ascertain whether the tip has passed through the opposite side of the vessel wall.

A variety of blood containment devices have been developed which are directed to the above problems. These devices provide a translucent or semi-translucent containment chamber. The plastic containment chamber has a catheter guideway lumen extending therethrough that allows insertion of a catheterization apparatus through the device. A valve is provided which prevents blood from escaping from the lumen and containment chamber, but allows passage of the catheterization apparatus.

When the needle is inserted into a patient's vein, the vascular blood containment device is positioned so as to facilitate filling of the blood containment chamber. Seal elements utilized with the blood containment device are adapted to permit filling of the blood containment chamber, but prevent the leakage of blood from the chamber. However, the configuration of existing devices and the positioning of the seals often requires that the vascular blood containment device be held at an unnatural angle so that the blood will fill the blood containment chamber as intended. For example, in some devices the blood containment chamber must be filled from the proximal end of the blood containment chamber. To function properly, the device must be held with the distal end positioned above the proximal end. As a result, for the device to function properly, the physician must utilize the device in an unnatural position.

Blood containment devices are utilized in hospital and other clinical settings where they must often be available at a moments notice. As with other medical devices, blood containment devices are often purchased in quantity. After they are purchased, the devices can be stored under a variety of conditions for variable amounts of time. The seal components and/or valve components of existing devices can be susceptible to failure subsequent to extreme storage conditions and/or prolonged storage periods.

BRIEF SUMMARY OF THE INVENTION

The present invention is directed to a vascular blood containment device for ascertaining whether a blood vessel has been accessed. The vascular blood containment device permits a user to determine whether the vessel accessed is a vein or artery and allows for the introduction of an enlongated medical instrument through the device. The vascular blood containment device includes an outer housing and an inner member. The inner member is positioned internal to the outer housing so as to form a blood containment chamber between the inner member and the outer housing.

According to one aspect of the present invention, a compression seal is positioned between the inner profile of the outer housing and the outer profile of the inner member. The compression seal is constructed of material adapted to permit the passage of gas when dry, but prevent the passage of liquid when contacted by liquid. The configuration of the compression seal allows blood to fill the blood containment chamber while preventing leakage of the chamber. The compression seal reliably prevents leakage of blood from the blood containment chamber subsequent to a variety of storage conditions.

According to another aspect of the present invention, a valve is provided that provides access to a blood vessel through the blood containment device while preventing blood from escaping from the blood containment device. The valve conforms to an inner profile formed around a bore in the distal end of the outer housing. The inner member exerts pressure on the valve to maintain contact between the valve and the outer housing. The configuration of the valve provides a reliable seal that prevents leakage of blood from the blood containment device.

According to another aspect of the present invention, the inner member and outer member both include apertures that permit blood to fill the blood containment chamber. The aperture of the inner member connects the lumen of the inner member with the blood containment chamber. The aperture of the outer housing connects the blood containment chamber with the exterior of the blood containment device. The compression seal is positioned adjacent the aperture of the outer housing and between the aperture of the inner member and the proximal end of the outer housing. The configuration of the apertures allows the blood containment chamber to fill in an optimal manner when the distal end of the blood containment device is positioned below the proximal end of the device.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
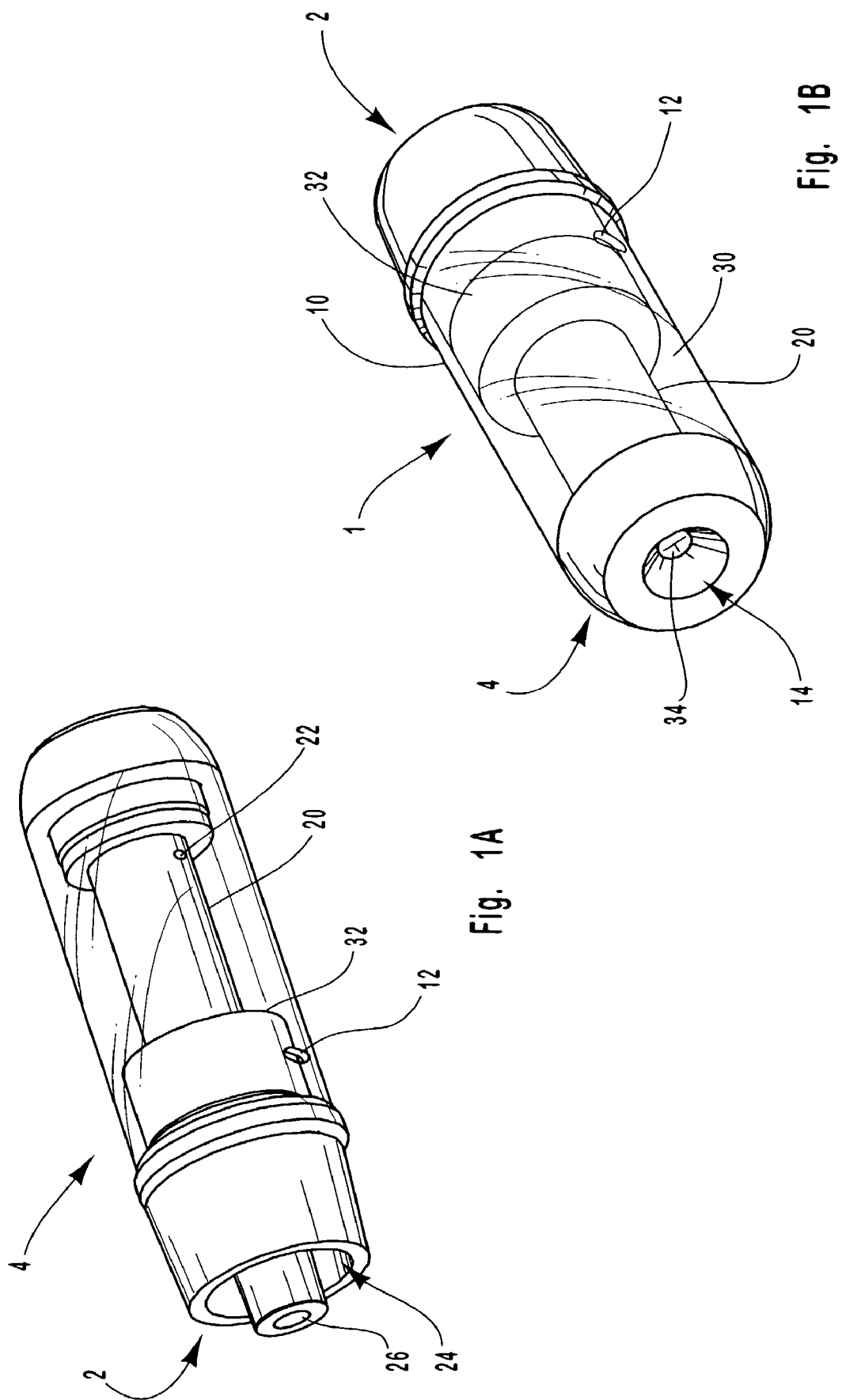
FIGS. 1A and 1B illustrates perspective views of the blood containment device according to one aspect of the present invention.

With reference now to FIG. 1 there is shown a perspective view of a blood containment device 1 according to one aspect of the present invention. Blood containment device 1 is configured to be coupled to a needle, trocar, or other apparatus used to access a patient's blood vessel. Blood containment device 1 allows a user to ascertain whether the needle has accessed a blood vessel. Once the blood vessel has been accessed, the blood containment chamber of blood containment device 1 begins to fill with blood from the blood vessel. By observing the flash rate with which the blood fills the blood containment chamber, the user can determine whether the vessel accessed is the vein or artery.

In the illustrated embodiment, blood containment device 1 comprises a proximal end 2, a distal end 4, an outer housing 10, an inner member 20, a blood containment chamber 30, a compression seal 32, and a valve 34. Proximal end 2 is coupled to the needle, trocar, or other device utilized to access the patient's blood vessel. Distal end 4 is positioned distally from the patient on the end of blood containment device 1 opposite proximal end 2. Distal end 4 provides a mechanism that permits a user to access the blood vessel utilizing a catheter, guide wire, or other mechanism.

Blood containment chamber 1 can have a variety of configurations without departing from the scope and spirit of the present invention. For example in one embodiment, the valve is positioned on the side of the blood containment device rather than at the distal end of the blood containment device. In another embodiment, the blood containment device has a rectangular configuration rather than a cylindrical configuration.

Outer housing 10 is coupled to inner member 20 such that a portion of inner member 20 is positioned internal to outer housing 10. Blood containment chamber 30 is formed between the portion of the inner member 20 and the outer housing 10. In the illustrated embodiment, outer housing 10 is comprised of a clear, or translucent material, permitting the user to ascertain the fill rate of blood filling blood containment chamber 30. By allowing the user to observe the rate at which blood fills the blood containment chamber 30, the user can determine the type of vessel accessed and whether the needle is appropriately positioned in the vessel.

A variety of types and configurations of outer housings can be utilized without departing from the scope or spirit of the present invention. For example, in one embodiment, the outer housing is comprised of an opaque material but includes a clear or translucent window for observing the fill rate of blood entering the blood containment chamber. In another embodiment, the outer housing is coupled to the inner member such that the entire inner member is positioned internal to the outer housing.

Outer housing 10 includes an aperture 12 and bore 14. Aperture 12 comprises a vent which permits the passage of gas from blood containment chamber 30. Aperture 12 allows gas to exit blood containment chamber 30 as the gas is displaced by blood entering the chamber. In the illustrated embodiment, aperture 12 is positioned in a slot. The slot prevents the user from inadvertently blocking the venting provided by aperture 12 when the user is grasping or manipulating blood containment device 1. Bore 14 is positioned at the distal end of outer housing. Bore 14 allows a user to insert a catheter, guide wire, or other device into a blood vessel through the blood containment device 1.

As previously discussed, inner member 20 is coupled to outer housing 10 such that a blood containment chamber 30 is formed between outer housing 10 and inner member 20. In the illustrated embodiment, inner member 10 includes an aperture 22, a needle engagement member 24, and a lumen 26. Aperture 22 is positioned near the distal end of inner member 20. Aperture 22 permits blood or other fluids to enter blood containment chamber 30 from lumen 26.

Needle engagement member 24 is coupled to the end of inner member 20. Needle engagement member 24 permits a needle, trocar, or other apparatus to be coupled to blood containment device 1. A variety of types and configurations of needle engagement members 24 can be utilized without departing from the scope or spirit of the present invention. For example, in one embodiment, the needle engagement member is a component separate from the inner member. In another embodiment, a needle engagement member is configured to provide a threaded coupling. In yet another embodiment, the needle engagement member provides a non-threaded coupling.

Lumen 26 is positioned internal to inner member 20 for substantially the entire length of inner member 20. Lumen 26 comprises a catheter guideway. Lumen 26 is in fluid communication with a blood vessel permitting a user to access the blood vessel. Blood containment chamber 30 is positioned between outer housing 10 and inner member 20. In illustrated embodiment, blood containment chamber 30 is defined by the inner profile of outer housing 10 and the outer profile of inner member 20 such that blood containment chamber 30 circumscribes inner member 30. Blood containment chamber 30 is placed in fluid communication with a blood vessel utilizing aperture 22 and lumen 26. Blood containment chamber 30 allows a user to ascertain whether the vessel accessed is a vein or artery. For example, in the illustrated embodiment, outer housing 10 is comprised of a clear, or translucent material, permitting the user to ascertain the fill rate of blood filling blood containment chamber 30. By allowing the user to observe the rate at which blood fills the blood containment chamber 30, the user can determine the type of vessel accessed. Additionally, the user can determine whether the tip of the needle, trocar, or other device is positioned internal to the blood vessel or has passed through the blood vessel into the surrounding interstitial tissue.

A variety of types and configurations of blood containment chambers can be utilized without departing from the scope and spirit of the present invention. For example, in one embodiment, the blood containment chamber comprises a narrow channel positioned between inner member 20 and outer housing 10. In an alternative embodiment, blood containment chamber is positioned between outer housing 20 and the entire outer profile of inner member 20.

Compression seal 32 is positioned between the inner profile of outer housing 10 and the outer profile of inner member 20. In one embodiment, compression seal 32 is comprised of a resilient material which allows compression seal 32 to be stretched and compressed. In the embodiment, compression seal has an inner diameter that is slightly smaller than the outer diameter of inner member 20 forming a fluid impermeable seal with the outer profile of inner member 10. In the embodiment, the outer diameter of compression seal 32 is slightly larger than the inner diameter of outer housing 10 so as to form a fluid impermeable seal with the inner profile of the outer housing 10.

Compression seal 32 is constructed of material that permits the passage of gas when dry, but prevents passage of fluid when contacted by fluid. As fluid fills blood containment chamber 30, the gas in chamber 30 is displaced by the fluid entering chamber 30. As the gas is displaced, compression seal 32 allows the gas to exit aperture 12 of outer housing 10. When blood containment chamber 30 is substantially full of fluid, the fluid contacts compression seal 32. When compression seal 32 is contacted by fluid, compression seal 32 prevents the passage of the fluid. By permitting passage of gas when dry but preventing passage of liquid when contacted by liquid, compression seal allows blood containment chamber 30 to be filled with fluid while also preventing leakage of the fluid from the blood containment device 1.

In one embodiment, compression seal 32 allows a user to determine the flashback rate with which blood previously filled blood containment chamber 30. In the embodiment, as compression seal 32 is contacted by fluid, the fluid permeates a given amount into compression seal 32. By observing the depth to which blood permeates the compression seal, a user can determine whether a vein or artery has been accessed. The depth to which the fluid permeates compression seal 32 is the result of factors such as the material from which compression seal 32 is constructed, the size of aperture 22 and/or aperture 12, the amount of pressure exerted by the fluid in chamber 30, and/or the rate with which fluid enters chamber 30 when compression seal 32 is first contacted by the fluid.

In one embodiment, compression seal 32 is configured to permit a user to observe the depth to which the fluid permeates seal 32. For example, the portion of seal 32 permeated by blood or other fluid turns red or is otherwise discolored. Because arterial pressure is greater than venous pressure, when an artery is accessed, blood will fill chamber 30 more quickly, will result in a greater pressure in chamber 30, and will permeate compression seal 32 to a greater depth, than when a vein is accessed. Because the depth with which the blood permeates seal 32 can be observed after blood containment chamber 30 is no longer filling, a user can ascertain whether a vein or artery was accessed even where the user did not observe the filling of chamber 30.

A variety of types and configurations of compression seals 32 can be utilized without departing from the scope and spirit of the present invention. For example, in one embodiment, the internal and external surfaces of compression seal have different profiles to conform to the different profiles of the outer profile of the inner member and the inner profile of the outer member. In another embodiment, the compression seal is only positioned adjacent the aperture of outer housing rather than circumscribing the entire circumference of the inner member.

Valve 34 is positioned between outer housing 10 and inner member 20. Valve 34 provides access to a blood vessel through the blood containment device 1 while also preventing blood from escaping from blood containment device 1. In the illustrated embodiment, valve 34 comprises a tricuspid valve. A variety of types and configuration of valve 34 can be utilized without departing from the scope or spirit of the present invention. For example, in one embodiment valve 34 is comprised of a resilient material such as silicon, rubber, or the like. In an alternative embodiment, valve 34 comprises a bicuspid valve.

Figure 2:
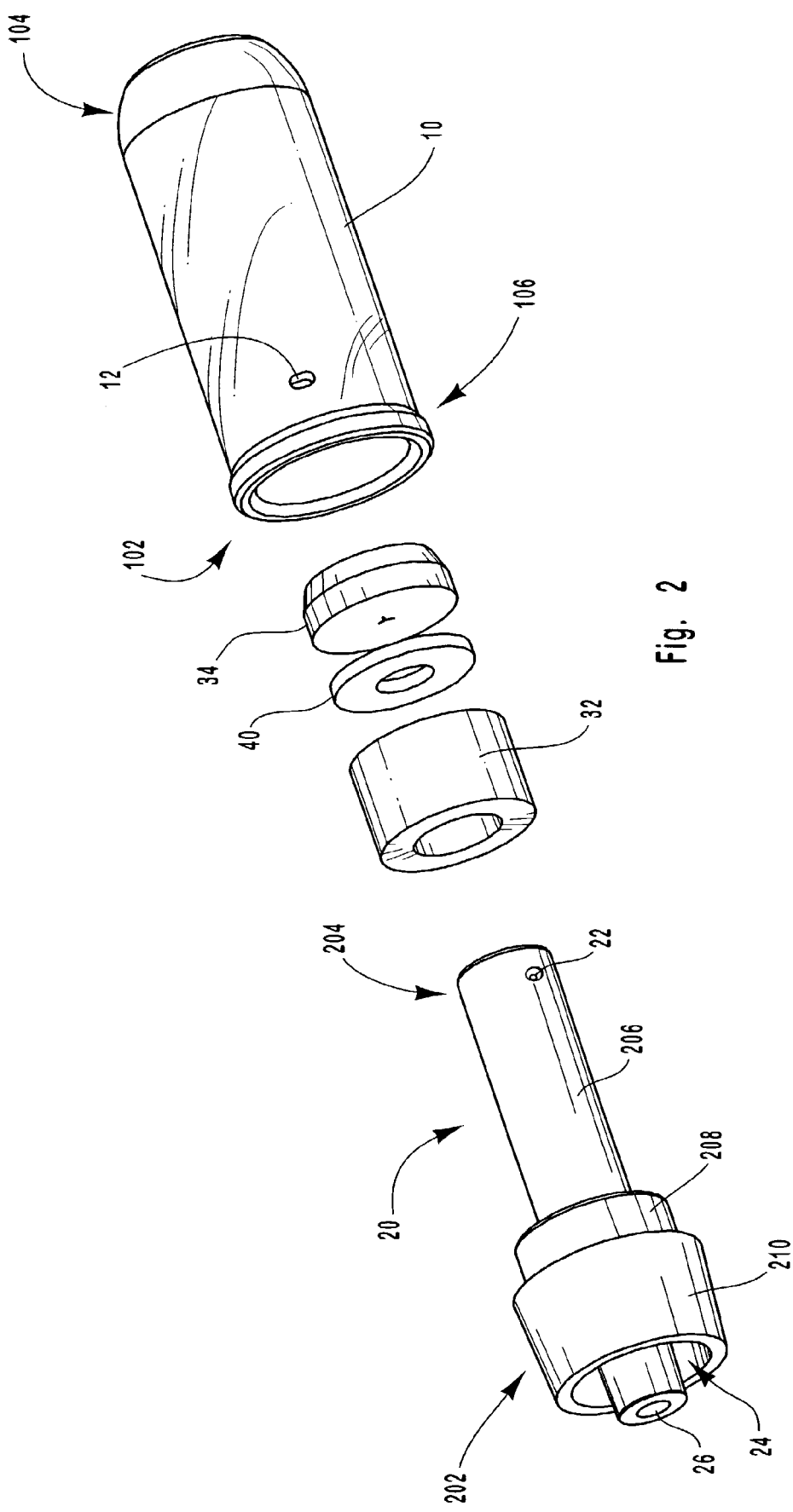
FIG. 2 illustrates an exploded view of the blood containment device according to one aspect of the present invention.

With reference now to FIG. 2, there is shown an exploded view of blood containment device 1 according to one aspect of the present invention. In the illustrated embodiment, there is shown outer housing 10, inner member 20, blood containment chamber 30, compression seal 32, valve 34, and a rigid member 40. Outer housing 10 includes a proximal end 102, a distal end 104, and a flare 106. Proximal end 102 is configured to permit inner member 20, compression seal 32, valve 34, and rigid member 40 to be placed inside outer housing 10. Distal end 104 includes a bore 14 permitting a user to insert a catheter, guide wire, or other device into a blood vessel through blood containment device 1.

Valve 34 comprises a resilient tricuspid member and is adapted to be positioned adjacent to the internal profile of distal end 104. Rigid member 40 comprises a washer positioned adjacent to valve 34. Rigid member 40 provides additional rigidity and support to valve 34 to prevent deformation of valve 34 and to ensure proper contact between valve 34 and the internal profile of distal end 104. Compression seal 32 is configured to be positioned between the internal profile of outer housing 10 and the outer profile of inner member 20.

In the illustrated embodiment inner member 20 includes a proximal end 202, a distal end 204, a shaft 206, a flange 208, and an end assembly 210. Proximal end 202 is configured to be positioned adjacent to a patient. Distal end 204 is positioned internal to outer housing 10 and in contact with rigid member 40. By contacting rigid member 40, distal end 204 ensures proper contact between valve 34 and the inner profile of distal end 104 of outer housing 10. Shaft 206 is positioned internal to outer housing 10. Flange 208 is positioned proximally to shaft 206. Flange 208 has a larger circumference than shaft 206. The circumference of the outer profile of flange 208 conforms to the inner diameter of proximal end 102 of outer housing 10 to provide a point of coupling therebetween. End assembly 210 is positioned proximally to flange 208. End assembly 210 has a greater circumference than flange 208 and is configured to be positioned proximally to outer housing 10.

The configuration of shaft 206, flange 208, and end assembly 210 facilitates the simple, efficient, and reliable manufacture of blood containment device 1. Once valve 34 and rigid member 40 are positioned internal to outer housing 10, compression seal 32 can be slid down shaft 206 until compression seal 32 contacts flange 208. Once compression seal 32 is positioned on shaft 206, shaft 206 and flange 208 can be inserted into proximal end 102 of outer housing 10 until proximal end 102 contacts end assembly 210. Once end assembly 210 contacts proximal end 102, distal end 204 is in contact with rigid member 40 ensuring adequate contact between valve 34 and the inner profile of distal end 104.

The inner profile of proximal end 102 conforms to the outer profile of flange 208 to form a point of coupling therebetween. Flare 106 provides additional rigidity to proximal end 102 to provide reliability and longevity to the point of coupling. As will be appreciated by those skilled in the art, the configuration of blood containment device 1 is not limited to the illustrated embodiment. A variety of types and configurations of components can be utilized without departing from the scope and spirit of the present invention. For example in one embodiment, the outer housing, the inner member, and the compression seal, have a square or rectangular configuration rather than a circular, or cylindrical configuration. In another embodiment, the distal end of the inner member contacts the valve directly, eliminating the need for a rigid member.

Figure 3:
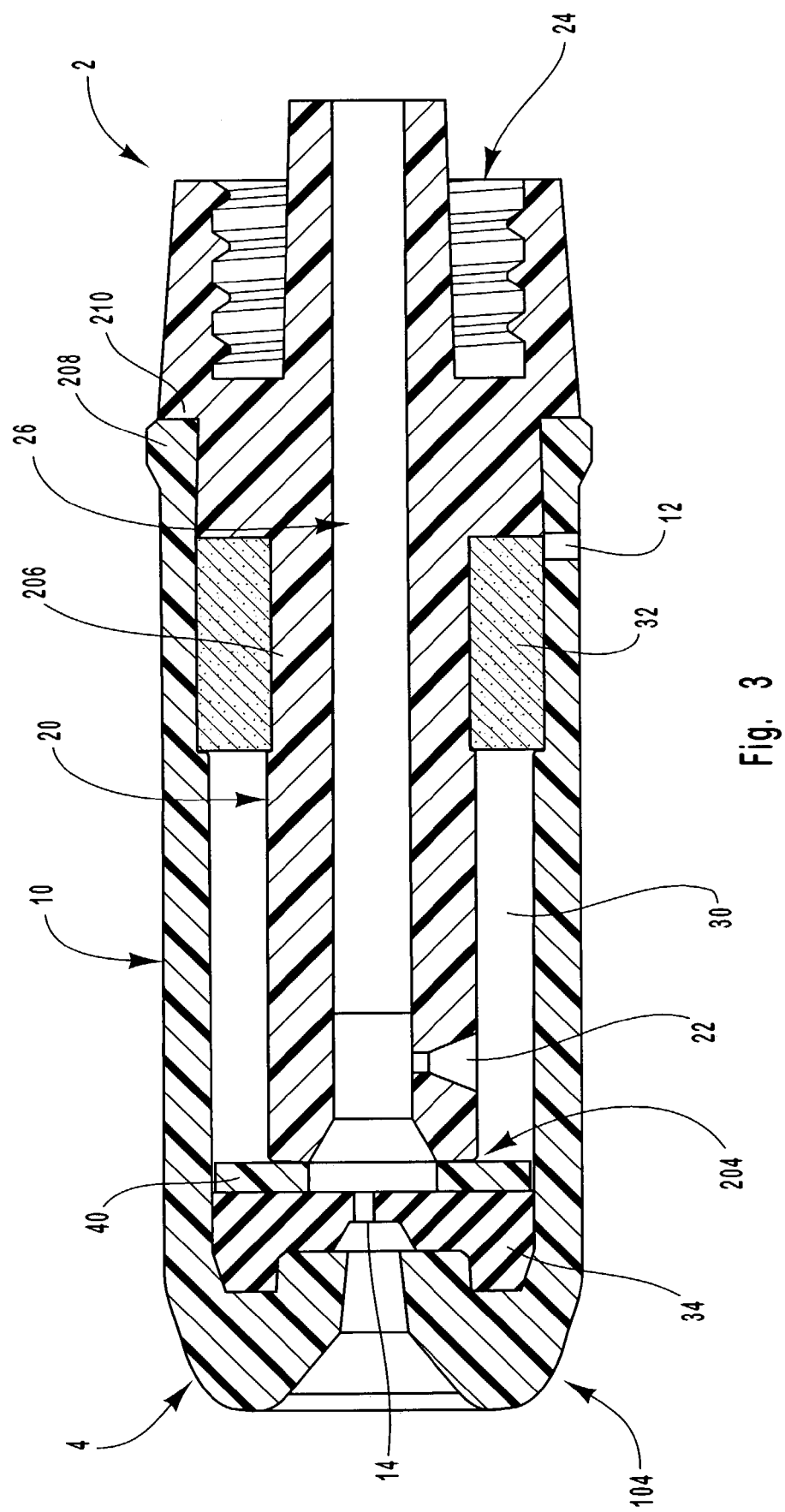
FIG. 3 illustrates a cross-sectional side view of the blood containment device according to one aspect of the present invention.

With reference now to FIG. 3, there is shown a cross-sectional side view of blood containment device 1, according to one aspect of the present invention. In the illustrated embodiment there is shown the juxtaposition of outer housing 10, inner member 20, blood containment chamber 30, compression seal 32, valve 34, and rigid member 40. As previously discussed, outer housing 10 is coupled to inner member 20 to form blood containment chamber 30 therebetween. Blood containment chamber 30 is formed between the outer profile of shaft 206 and the inner profile of outer housing 10.

Valve 34 and rigid member 40 are positioned between the inner profile of distal end 104 of outer housing 10 and distal end 204 of inner member 20. Rigid member 40 is positioned adjacent to distal end 204 of inner member 20. Valve 34 is positioned adjacent to the internal profile of distal end 104 of outer housing 10. In the illustrated embodiment, the inner profile of distal end 104 is such that an inner diameter is formed around bore 14. Valve 34 has a distal surface and a proximal surface. The distal surface of valve 34 conforms to the inner profile of distal end 104 of outer housing 10 so as to create a seal with the inner profile formed around bore 14. The seal formed between the distal surface of valve 34 and the inner diameter formed around bore 14 prevents leakage of fluids from blood containment device 1 even where blood containment device is subject to adverse conditions or is stored for prolonged periods.

Compression seal 32 is positioned between the inner profile of outer housing 10 and the outer profile of inner member 20. Compression seal 32 is positioned adjacent aperture 12 of outer housing 10 and between aperture 22 of inner member 10 and proximal end 102 of the outer housing 10. Compression seal 32 permits passage of gas from blood containment chamber 30 to the exterior of blood containment device 1. Additionally, compression seal forms a fluid impermeable barrier between blood containment chamber 30 and the exterior of blood containment device 1. Aperture 22 of inner member 20 allows fluid to pass from lumen 26 to blood containment chamber 30. Aperture 12 of outer housing 10 allows gases to pass from blood containment chamber to the exterior of blood containment device 1.

Needle engagement member 24 permits a needle, trocar, or other apparatus to be coupled to blood containment device 1. In the illustrated embodiment, needle engagement member 24 includes an inner diameter and an outer threaded diameter. The outer threaded diameter engages the threads of the apparatus that is to be coupled to blood containment device 1. The inner diameter reinforces contact between the outer threaded diameter and the apparatus to ensure a reliable and fluid impermeable seal therewith.

Figure 4A:
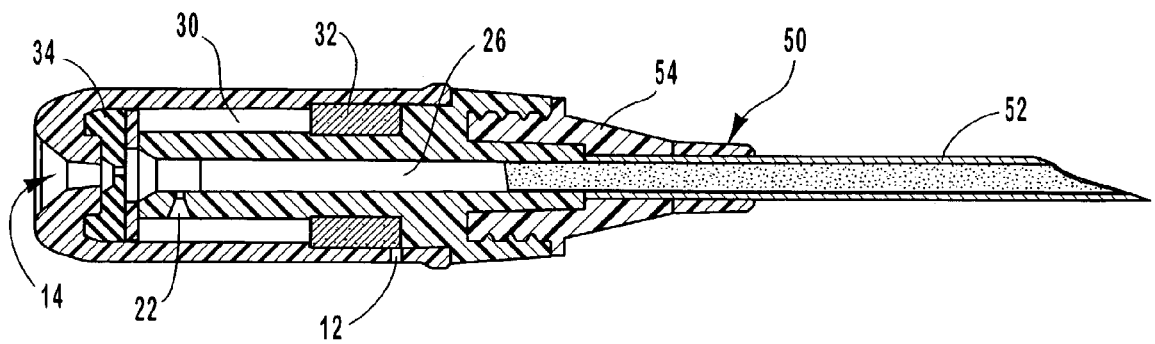
FIGS. 4A, 4B, and 4C illustrate cross-sectional side views of the blood containment device depicting the manner in which blood fills the blood containment chamber.
Figure 4B:
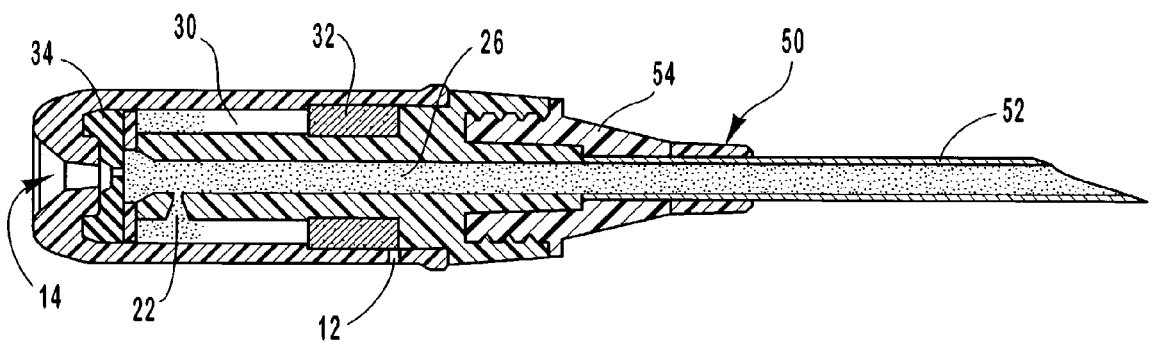
Figure 4C:
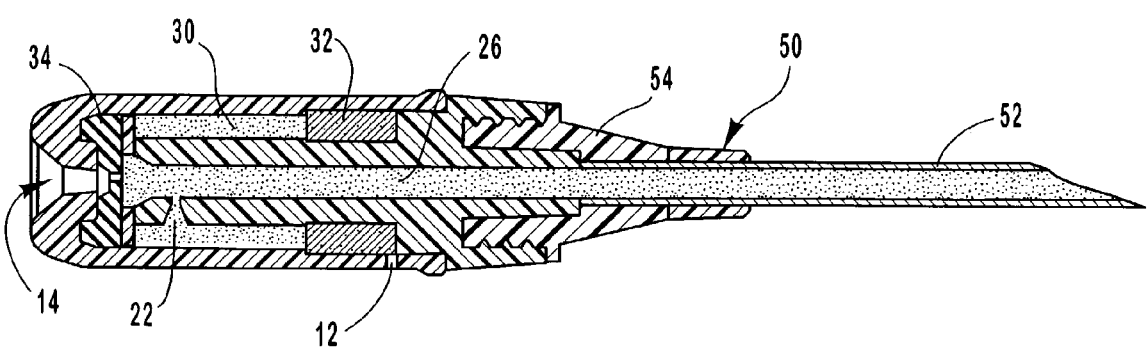

With reference now to FIGS. 4A, 4B, and 4C, there is shown a cross sectional side view of blood contain device 1 according to one aspect of the present invention. FIGS. 4A, 4B, and 4C illustrate the manner in which blood containment device 1 permits a user to ascertain whether a blood vessel has been accessed and whether the vessel accessed is a vein or artery.

There is shown a needle assembly 50 coupled to blood containment device 1. Needle assembly 50 permits a user to access a patient's blood vessel. Needle assembly 50 comprises an assembly base 52 and a needle 54. Assembly base 52 provides a mechanism for attaching needle assembly 50 to needle engagement member 24 of blood containment device 1. Additionally, assembly base 52 provides the strength and support necessary for proper functioning of needle 54. Needle 54 is inserted through a patient's interstitial tissue to access the patient's blood vessel.

With reference now to FIG. 4A, there is shown needle 54, assembly base 52, and lumen 26. Needle 54, assembly based 52, and a portion of lumen 26 are filled with blood. The degree to which blood fills lumen 26 indicates that the blood vessel has just been penetrated. The blood has just begun to flow from the blood vessel into the blood containment device 1.

In FIG. 4B, lumen 26 is completely filled with blood while blood containment chamber 30 is beginning to fill with blood as well. As can be seen from the movement of blood from FIG. 4A to FIG. 4B, the blood substantially fills lumen 26 before entering blood containment chamber through aperture 22. As blood is filling lumen 26, the blood contacts valve 34. Valve 34 prevents leakage of blood from bore 14. The blood is then forced from lumen 26, through aperture 22, and into blood containment chamber 30.

As the blood fills lumen 26 and blood containment chamber 30, the blood displaces gases in lumen 26 and blood containment chamber 30. The gases that are displaced from lumen 26 and blood containment chamber 30 pass through compression seal 32 and aperture 12 to the exterior of blood containment device 1. Compression seal 32 is positioned adjacent to aperture 12. The position of compression seal 32 relative to aperture 12 ensures that all substances passing through aperture 12 pass through compression seal 32.

Compression seal 32 is positioned between aperture 22 of inner member 20 and the proximal end 102 of outer housing. In other words, aperture 22 of inner member 20 is positioned distally to compression seal 32. In the illustrated embodiment, aperture 22 is located at or near the distal end 204 of inner member 20. The position of aperture 22 relative to compression seal 32 and aperture 12 allows the distal end 4 of blood containment device 1 to be held lower than the proximal end 202 of blood containment device 1.

FIG. 4C shows lumen 26 and blood containment chamber 30 completely filled with blood. Compression seal 32 prevents leakage of blood from blood containment device 1 when compression seal 32 is contacted by the blood filling blood containment chamber 22. As previously discussed, compression seal 32 is constructed of material adapted to permit the passage of gas to the exterior of blood containment device 1 when compression seal is dry, but prevent the passage of liquid when the compression seal 32 is contacted by liquid.

A variety of types and configurations of blood containment chamber can be utilized without departing from the scope or the spirit of the present invention. For example, in one embodiment, aperture 22 is located closer to the middle of inner member 20 rather than near distal end 204 of inner member 20. In another embodiment, compression seal 32 does not entirely circumscribe inner member 20 but only contacts the portion of inner member 20 corresponding with aperture 12 of outer housing 10. In another embodiment, blood containment device 1 is configured to be utilized with fluids other than blood. As will be appreciated by those skilled in the art, the size, volume, and diameter of lumen 26, aperture 22, and aperture 12, as well as the properties of compression seal 32 can be modified to change the flash rate of blood or other fluid entering the blood containment device 1. The flash rate can be modified to accommodate different viscosities of fluid, different applications in which the blood containment device is utilized, varying requirements of the medical procedures, and/or according to the needs of the patient on which a procedure is to be performed.

Figure 5A:
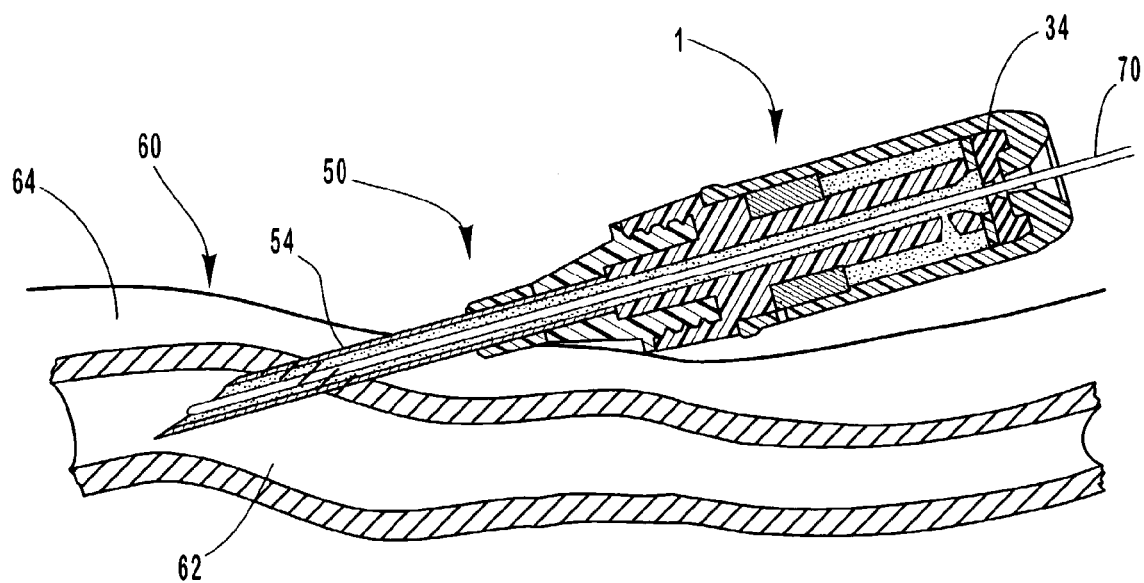
FIGS. 5A, 5B, and 5C, show cross-sectional side views of the blood containment device illustrating the manner in which a guide wire can be inserted through the blood containment device.
Figure 5B:
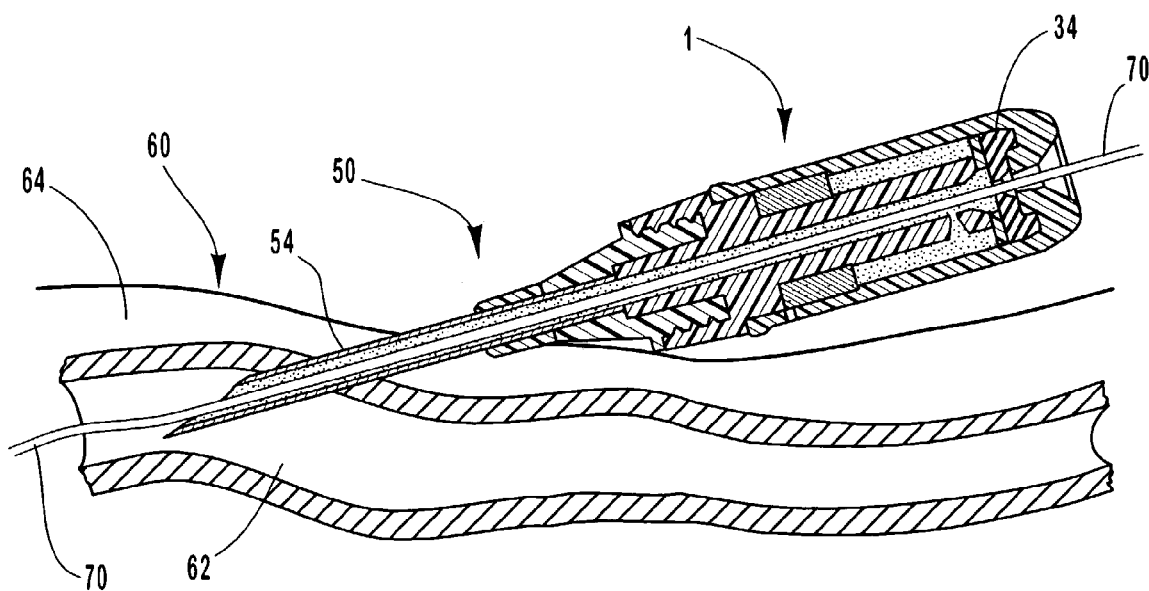
Figure 5C:
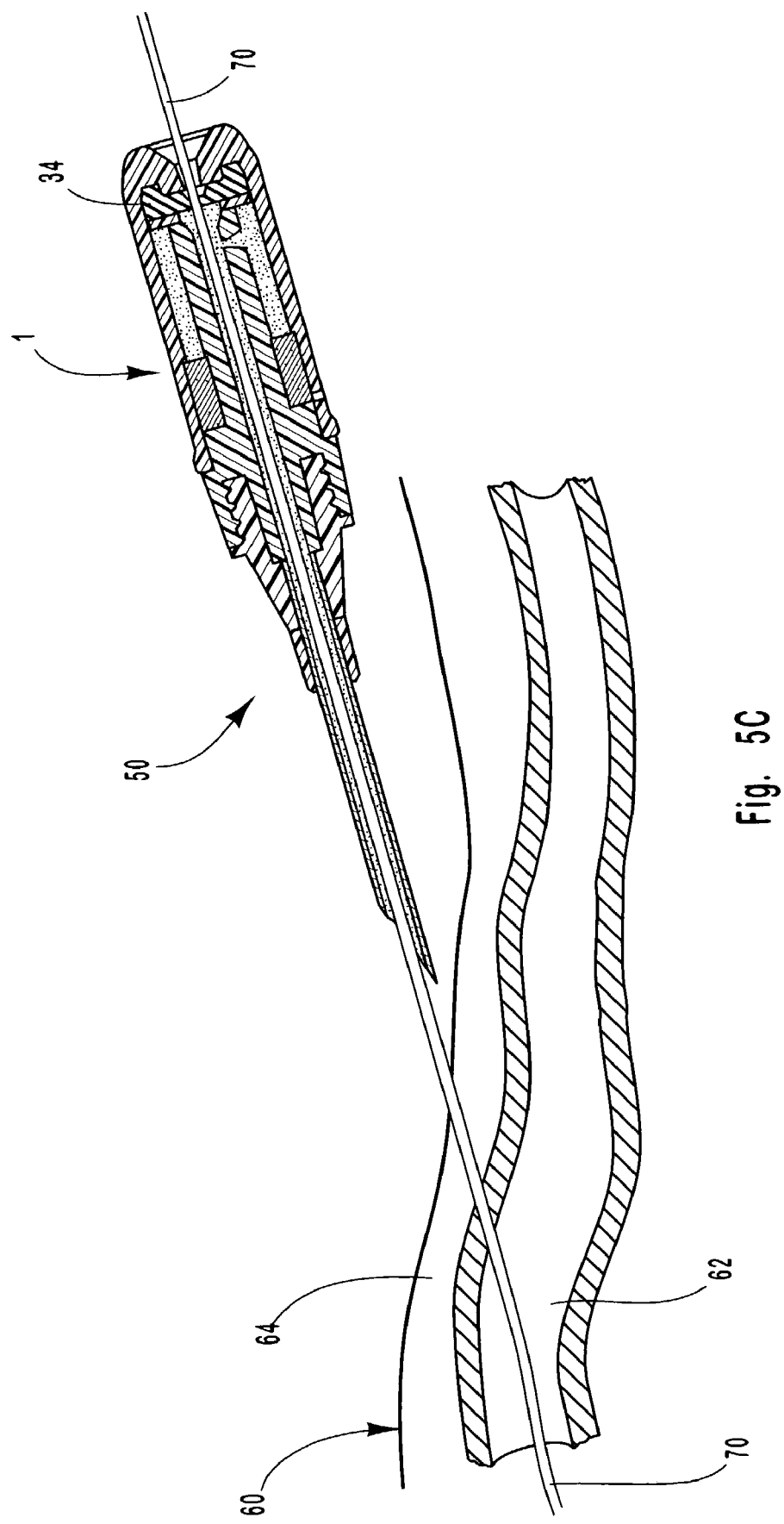

With reference now to FIG. 5A, 5B, and 5C, there is shown the manner in which blood containment device 1 can be utilized. There is shown a patient 60 having a blood vessel 62 and interstitial tissue 64. In FIG. 5A, needle 54 is positioned internal to blood vessel 62. Blood vessel 62 has been accessed through interstitial tissue 64. By observing the flash rate of the blood filling the blood containment chamber 30, a user identifies blood vessel 62 as a vein or artery. If the vessel accessed is the type of vessel desired to be utilized in the medical procedure being performed, the user will proceed with the procedure. There is shown a guide wire 70 that is being inserted through valve 34 and into lumen 26 of blood containment device 1. Valve 34 is deformable to permit blood containment device 1 and guide wire 70 to be moved relative to one another while preventing leakage of fluid from lumen 26.

In FIG. 5B, guide wire 70 has been threaded through the entire length of both blood containment device 1 and needle assembly 50. The end of guide wire 70 is positioned in blood vessel 62. In FIG. 5C, guide wire 70 remains in blood vessel 62 while needle 54 has been withdrawn from patient 60. As will be appreciated by those skilled in the art, a variety of types and configurations of apparatuses can be inserted through the lumen of blood containment device 1 without departing from the scope or spirit of the present invention.

Figure 6A:
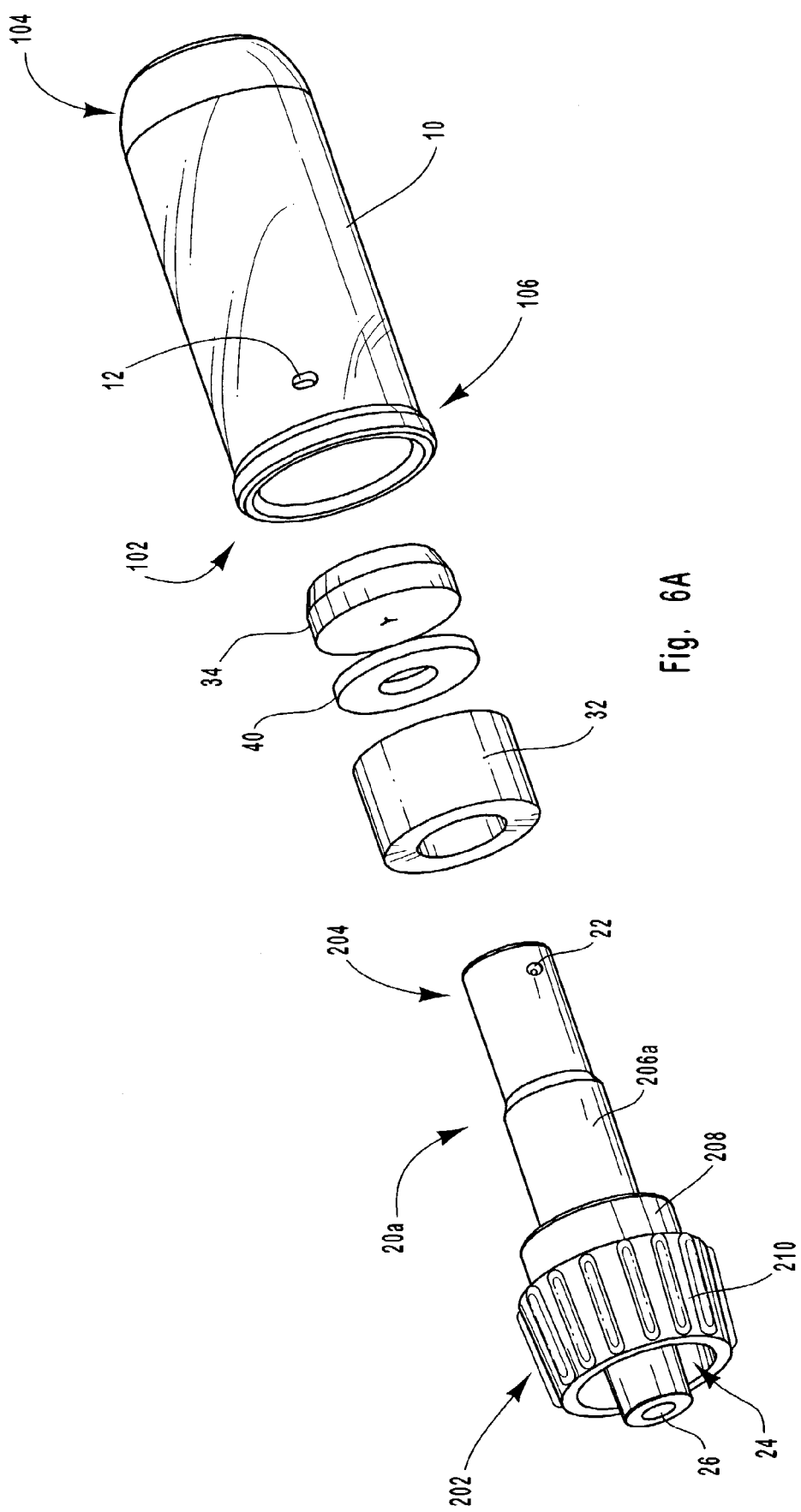
FIGS. 6A and 6B illustrate an alternative embodiment of the blood containment device having a variable diameter inner member.
Figure 6B:
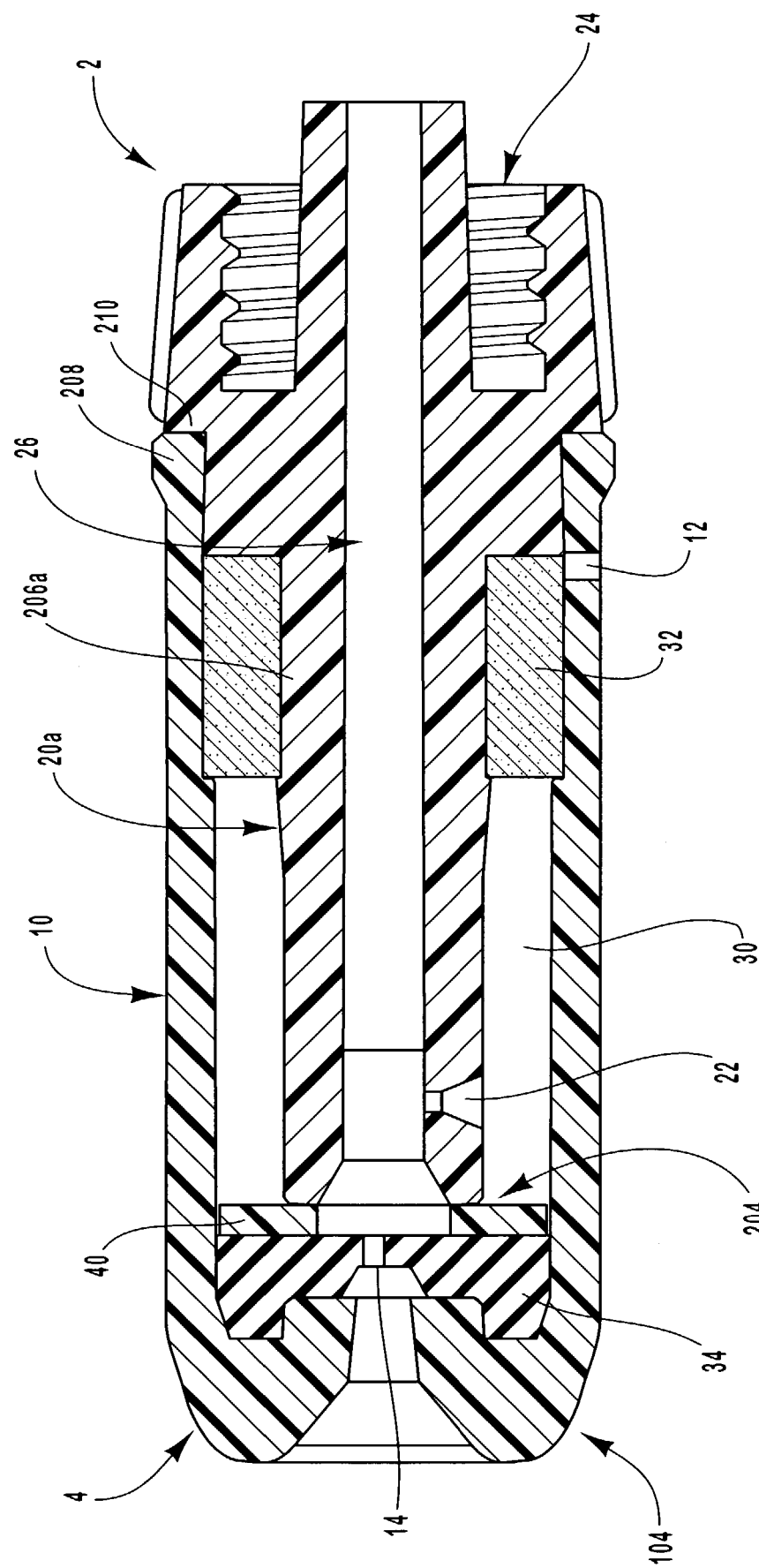

FIG. 6A and 6B illustrate an alternative embodiment of blood containment device. In the illustrated embodiment, shaft 206a of inner member 20a has a variable width. The proximal portion of shaft 206a has a greater diameter than the distal portion of shaft 206a. Compression seal 32 forms a fluid impermeable seal with the proximal portion of shaft 206a while encountering little or no resistance when sliding over the distal portion of shaft 206a. This allows the distal portion of shaft 206a to pass easily inside compression seal 32 without causing damage or obstruction to seal 32 while permitting seal 32 to form a seal over the outer diameter of the proximal portion of shaft 206a.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A vascular blood containment device for ascertaining whether a blood vessel has been accessed and permitting a user to determine whether the vessel accessed is a vein or artery, the blood containment device comprising:
   an outer housing, the outer housing having a clear portion permitting the user to view inside the outer housing;
   an inner member having at least a portion thereof positioned internal to the outer housing so as to form a blood containment chamber between the inner member and the outer housing, the clear portion surrounding the blood containment chamber so as to permit a user to observe a rate at which blood fills the blood containment chamber such that the user can determine whether an accessed blood vessel is a vein or artery based on the fill rate;
   the inner member comprising a first aperture disposed at a distal end of the blood containment chamber, and through which blood enters the blood containment chamber;
   the outer housing comprising a second aperture disposed at a proximal end of the blood containment chamber and through which air is vented as blood fills the blood containment chamber; and
   a compression seal positioned between the inner profile of the outer housing and outer profile of the inner member and adjacent to the venting aperture and such that the compression seal is disposed against both the inner profile of the outer housing and the outer profile of the inner member, the compression seal being constructed of material adapted to permit passage of gas through the compression seal and out the second aperture when dry but prevent passage of liquid through the compression seal when contacted by liquid.

2. The vascular blood containment device of claim 1, wherein the compression seal prevents leakage of fluid from the point of coupling between the outer housing and inner member.

3. The vascular blood containment device of claim 1, wherein the compression seal is positioned adjacent the proximal end of the blood containment chamber.

4. The vascular blood containment device of claim 1, wherein the compression seal permits a user to ascertain whether the blood vessel accessed was a vein or artery based on the depth to which blood permeated the compression seal.

5. The vascular blood containment device of claim 1, wherein the compression seal is comprised of a resilient material that allows the compression seal to be stretched and compressed.

6. The vascular blood containment device of claim 5, wherein the compression seal has an inner profile that is slightly smaller than the outer profile of the inner member so as to form a fluid impermeable seal with the outer profile of the inner member.

7. The vascular blood containment device of claim 1, wherein the outer housing comprises a cylindrical sleeve.

8. The vascular blood containment device of claim 7, wherein the inner member comprises a shaft, a flange, and an end assembly.

9. The vascular blood containment device of claim 8, wherein the blood containment chamber is positioned between the outer housing and the shaft of the inner member.

10. The vascular blood containment device of claim 9, wherein the compression seal is positioned between an inner diameter of the outer housing and an outer diameter of the inner member.

11. The vascular blood containment device of claim 10, wherein the outer diameter of the compression seal is slightly larger than the inner diameter of the outer housing so as to form a fluid impermeable seal with the inner profile of the outer housing.

12. A vascular blood containment device for ascertaining whether a blood vessel has been accessed the blood containment device comprising:
   an outer housing having a clear portion permitting a user to view inside the outer housing;
   an inner member having at least a portion thereof positioned internal to the outer housing so as to form a blood containment chamber between the outer housing and the inner member, the clear portion surrounding the blood containment chamber so as to permit a user to observe the rate at which blood fills the blood containment chamber such that the use can determine whether an accessed blood vessel is a vein or artery based on the fill rate, the inner member comprising;
   a lumen; and
   an a first aperture disposed at a distal end of the blood containment chamber, and through which blood enters the blood containment chamber from the lumen; and
   the outer housing comprising a second aperture disposed at a proximal end of the blood containment chamber and through which air is vented as blood fills the blood containment chamber; and
   a seal positioned adjacent to the second aperture, and also being positioned between the first aperture and the proximal end of the blood containment chamber and in such a manner that the seal is disposed against both the inner profile of the outer housing and the outer profile of the inner member.

13. The vascular blood containment device of claim 12, wherein the second aperture is positioned near the proximal end of the outer housing.

14. The vascular blood containment device of claim 13, wherein the first aperture is positioned near the distal end of the inner member.

15. The vascular blood containment device of claim 12, wherein blood substantially fills the lumen before entering the blood containment chamber through the first aperture.

16. The vascular blood containment device of claim 15, wherein the position of the seal relative to the second aperture ensures that all substances passing through the second aperture pass through the seal.

17. The vascular blood containment device of claim 12, wherein the first aperture is positioned distally to the seal.

18. The vascular blood containment device of claim 12, wherein the first aperture is positioned distally to the second aperture.

19. The vascular blood containment device of claim 12, wherein the position of the first aperture relative to the seal and the second aperture allows proper filling of the blood containment chamber when the distal end of the blood containment chamber is held lower than a the proximal end of the blood containment chamber.

20. The vascular blood containment device of claim 12, wherein the configuration of the blood containment device ensures that the blood containment chamber fills with blood before the blood contacts the compression seal.

21. A vascular blood containment device for ascertaining whether a blood vessel has been accessed and permitting a user to view a flashrate with which the blood fills a blood containment chamber so as to determine whether the vessel accessed is a vein or artery, the blood containment device comprising:
   an outer housing having a clear portion permitting the user to view inside the outer housing and an access bore therethrough;
   an inner member having at least a portion thereof positioned internal to the outer housing so as to form a blood containment chamber between the outer housing and the inner member, the clear portion surrounding the blood containment chamber so as to permit a user to observe a rate at which blood fills the formed containment chamber such that the user can determine whether an accessed blood vessel is a vein or artery, the inner member comprising:
   a lumen; and
   first aperture disposed at a distal end of the blood containment chamber and through which blood enters the blood containment chamber from the lumen; and
   the outer housing comprising a second aperture disposed at a proximal end of the blood containment chamber and through which air is vented as blood fills the blood containment chamber; and
   a compression seal positioned between the outer diameter of the inner member and the inner diameter of the outer housing, and further being positioned between the —first aperture and the proximal end of the —blood containment chamber and such that the compression seal is disposed against both the inner profile of the outer housing and the outer profile of the inner member, the compression seal being constructed of material adapted to permit passage of gas from the blood containment chamber to the exterior of the blood containment device through the second aperture when the compression seal is dry but also being adapted to prevent passage of liquid when the compression seal is contacted by liquid; and
   a valve having a distal valve surface and proximal valve surface, the distal valve surface conforming to and being disposed within the inner profile of the distal end of the blood containment chamber so as to create a seal with the inner diameter of the outer housing, the configuration of the valve providing access to a blood vessel while preventing blood from escaping from the blood containment device.

22. The vascular blood containment device of claim 21, wherein one or more of: the diameter of the access bores; the volume of the blood containment chamber; and the material properties of the compression seal can be varied to control the flashrate with which the blood fills the blood containment device.

23. The vascular blood containment device of claim 21, wherein the inner member includes an end assembly.

24. The vascular blood containment device of claim 23, wherein the end assembly includes a needle engagement member for coupling a needle assembly to the vascular containment device.

25. The vascular blood containment device of claim 24, wherein the needle engagement member includes an inner diameter and an outer threaded diameter.

26. The vascular blood containment device of claim 1, wherein the compression seal circumferentially extends around the entire diameter of the inner member.

27. The vascular blood containment device of claim 21, wherein the valve is disposed between the inner member and the outer housing.

* * * * *

UNITED STATES PATENT AND TRADEMARK OFFICE
CERTIFICATE OF CORRECTION

PATENT NO. : 7,261,703 B2
APPLICATION NO. : 10/424886
DATED : August 28, 2007
INVENTOR(S) : Fred P. Lampropoulos et al.

It is certified that error appears in the above-identified patent and that said Letters Patent is hereby corrected as shown below:

Column 1, Line 12 reads, "...enlongated medical instrument..." which should read -- ...elongated medical instrument... --

Column 2, Lines 30-31 read, "...of an enlongated medical instrument..." which should read -- ...of an elongated medical instrument... --

Column 3, Line 21 reads, "FIGS. 1A and 1B illustrates perspective..." which should read -- FIGS. 1A and 1B illustrate perspective... --

Column 8, Line 15 reads, "...shown a cross sectional side view..." which should read -- ...shown a cross-sectional side view... --

Signed and Sealed this

Twenty-third Day of September, 2008

JON W. DUDAS
*Director of the United States Patent and Trademark Office*